United States Patent
Duncan et al.

(10) Patent No.: US 7,294,740 B2
(45) Date of Patent: Nov. 13, 2007

(54) PROCESS FOR THE SYNTHESIS OF N-ACYL-2-AMINO-4-ALKOXY-5-NITROBENZOIC ACIDS

(75) Inventors: Scott Mason Duncan, Madison, WI (US); Augustine Tobi Osuma, Canton, MI (US); Sylvain Daigneault, Quebec (CA); Michel Bernatchez, Montreal (CA)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 11/804,509

(22) Filed: May 18, 2007

(65) Prior Publication Data

US 2007/0219394 A1 Sep. 20, 2007

Related U.S. Application Data

(62) Division of application No. 10/358,847, filed on Feb. 5, 2003, now Pat. No. 7,227,037.

(60) Provisional application No. 60/354,777, filed on Feb. 5, 2002.

(51) Int. Cl.
*C07C 51/16* (2006.01)
*C07C 205/00* (2006.01)

(52) U.S. Cl. .................. 562/407; 562/411; 562/434
(58) Field of Classification Search .................. None
See application file for complete search history.

(56) References Cited

U.S. PATENT DOCUMENTS 6,002,008 A 12/1999 Wissner et al.
7,227,037 B2 * 6/2007 Duncan et al. ............. 564/134

FOREIGN PATENT DOCUMENTS

WO WO 01/68186 9/2001

OTHER PUBLICATIONS

Ona, a., Chem. Ind. (London), 4, 130, 1982.
Lee, C. et al., Journal Org. Chem., 1989, 54, pp. 3744-3747.
Larock, R., *Comprehensive Organic Transformations, A Guide to Functional Group Preparations*, VCH Publishers, New York, 1989, p. 823.

* cited by examiner

*Primary Examiner*—Sikarl A. Witherspoon
(74) *Attorney, Agent, or Firm*—Stephen E. Johnson

(57) ABSTRACT

The invention claimed herein provides a process to oxidize N-(5-alkoxy-2-methyl-4-nitrophenyl)acetamides to N-acyl-2-amino-4-alkoxy-5-nitrobenzoic acids using potassium permanganate in the presence of magnesium sulfate in aqueous sulfolane or aqueous pyridine.

12 Claims, No Drawings

PROCESS FOR THE SYNTHESIS OF N-ACYL-2-AMINO-4-ALKOXY-5-NITROBENZOIC ACIDS

CROSS REFERENCE TO RELATED APPLICATIONS

This application claims priority from copending provisional application No. 60/354,777 filed on Feb. 5, 2002, and non-provisional application Ser. No. 10/358,847 filed Feb. 5, 2003, the entire disclosure of which is hereby incorporated by reference.

BACKGROUND OF THE INVENTION

This invention relates to a process for the synthesis of N-acyl-2-amino-4-alkoxy-5-nitrobenzoic acids by the oxidation of N-(5-alkoxy-2-methyl-4-nitrophenyl)acetamides using potassium permanganate in aqueous solvent mixtures.

Potassium permanganate is a widely used reagent for the oxidation of benzylic carbon atoms to the corresponding carboxylic acid. However, oxidations do not always work well for substrates having limited water solubility and furthermore, potassium permanganate has limited solubility in organic solvents. The problem with insolubility has been addressed to some extent by the use of biphasic conditions employing water and either benzene or a hydrocarbon solvent as the organic phase, or, alternatively by using a phase transfer catalyst. Unfortunately, many organic compounds or substrates have poor solubility in either water or hydrocarbon solvents. The limited contact between the oxidant and the substrate results in long reaction times, poor yields and the formation of contaminates which make purification difficult. Further, many typical organic solvents cannot be used as a co-solvent with potassium permanganate because being such a potent oxidant, the organic solvents are themselves oxidized, leading to diverse and complicated reaction mixtures. The use of a phase transfer catalyst can lead to further purification problems.

The N-acyl-2-amino-4-alkoxy-5-nitrobenzoic acids that are obtained according to the process of this invention are useful intermediates to produce 3-cyanoquinolines. The 3-cyano quinolines are used in the synthesis, as described in U.S. Pat. No. 6,002,008, the disclosure of which is hereby incorporated by reference in its entirety, of certain protein tyrosine kinase (PTK) inhibitors useful for the treatment of cancer. The toluidines that are required to produce the desired N-acyl-2-amino-4-alkoxy-5-nitrobenzoic acids have very poor solubility in water. The problem of poor water solubility contributes to incomplete reactions and variable yields when performing the oxidation in water alone with potassium permanganate as the oxidizing agent in the presence of magnesium sulfate. The accelerated decomposition of potassium permanganate, under aqueous conditions requires a very large excess of the oxidant resulting in large volumes of inorganic waste. Additionally, the low solubility of both the substrate and the oxidant in water contribute to the inefficiency of the total process by requiring high dilutions (>40:1).

It is also known that certain substrates, which include derivatives of toluidine such as N-(5-alkoxy-2-methyl-4-nitrophenyl)acetamides, can catalyze the decomposition of potassium permanganate. As mentioned above, solubility and decomposition problems contribute to the need for a large excess of potassium permanganate. Also, isolating and solving problems of potassium permanganate oxidations are difficult because of the subtleties of the equilibrium between the various oxidation states of manganese.

The N-(5-alkoxy-2-methyl-4-nitrophenyl)acetamides used as the oxidation substrates are prepared with acetic anhydride using conditions well described in the art (e.g., A. Ono in Chem. Ind.(London), 4, 130, 1982). As described, adding N-(5-alkoxy-2-methyl-4-nitrophenyl)acetamides as a solid to an aqueous mixture of the potassium permanganate and magnesium sulfate at about 80-90° C. followed by heating the reaction mixture to reflux for 1 hour further required adding additional potassium permanganate and magnesium sulfate as necessary at 30 minute intervals to fully oxidize the N-(5-alkoxy-2-methyl-4-nitrophenyl)acetamides. Typically, 4 to 5 equivalents of the oxidant are necessary under these conditions. The yield of the oxidation under totally aqueous conditions is however improved by adding the substrate as a hot slurry in water. However, the disadvantage to this procedure becomes apparent on larger scale when one needs to prepare the substrate as a hot slurry in water followed by adding the slurry to the aqueous potassium permanganate.

It is, therefore, an object of the present invention to provide a new process for the preparation of N-acyl-2-amino-4-alkoxy-5-nitrobenzoic acids which avoids the solubility problems associated with potassium permanganate in organic solvents and to additionally solve the problem of needing a large excess of potassium permanganate.

Thus, there is a need in the art for a process which overcomes the problems of solubility and the need for excess potassium permanganate when oxidizing, in particular, toluidines.

Those and other objects of the present invention will become more apparent from the detailed description thereof set forth below.

SUMMARY OF THE INVENTION

The present invention provides a new process for the preparation of N-acyl-2-amino-4-alkoxy-5-nitrobenzoic acids having the structural formula

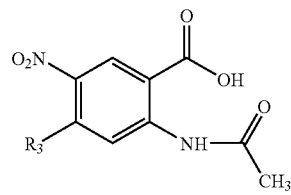

wherein:

R$_3$ is —OR and

R is alkyl of 1 to 3 carbon atoms;

which process comprises oxidizing N-(5-alkoxy-2-methyl-4-nitrophenyl)acetamides having the formula

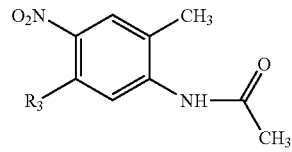

where

R$_3$ is —OR; and

R is alkyl of 1 to 3 carbon atoms;

with potassium permanganate in an aqueous solvent mixture to afford N-acyl-2-amino-4-alkoxy-5-nitrobenzoic acids after acidification. The oxidation is generally carried out in solution in a solvent system comprising water and a cosolvent, normally an organic cosolvent.

The invention also provides a process for the manufacture of a compound having the formula I

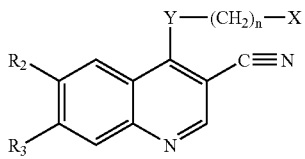

I wherein:

X is cycloalkyl of 3 to 7 carbon atoms, which may be optionally substituted with one or more alkyl of 1 to 6 carbon atom groups; or is a pyridinyl, pyrimidinyl, or phenyl ring; wherein the pyridinyl, pyrimidinyl, or phenyl ring may be optionally mono-, di-, or tri-substituted with a substituent selected from the group consisting of halogen, alkyl of 1-6 carbon atoms, alkenyl of 2-6 carbon atoms, alkynyl of 2-6 carbon atoms, azido, hydroxyalkyl of 1-6 carbon atoms, halomethyl, alkoxymethyl of 2-7 carbon atoms, alkanoyloxymethyl of 2-7 carbon atoms, alkoxy of 1-6 carbon atoms, alkylthio of 1-6 carbon atoms, hydroxy, trifluoromethyl, cyano, nitro, carboxy, carboalkoxy of 2-7 carbon atoms, carboalkyl of 2-7 carbon atoms, phenoxy, phenyl, thiophenoxy, benzoyl, benzyl, amino, alkylamino of 1-6 carbon atoms, dialkylamino of 2 to 12 carbon atoms, phenylamino, benzylamino, alkanoylamino of 1-6 carbon atoms, alkenoylamino of 3-8 carbon atoms, alkynoylamino of 3-8 carbon atoms, and benzoylamino;

R$_3$ is —OR;

R is alkyl of 1 to 3 carbon atoms;

n is 0-1;

Y is —NH—, —O—, —S—, or —NR$_{10}$—;

R$_{10}$ is alkyl of 1-6 carbon atoms;

R$_2$ is

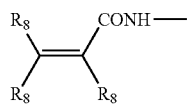

in which each R$_8$ is independently selected from hydrogen, alkyl of 1-6 carbon atoms, aminoalkyl of 1-6 carbon atoms, N-alkylaminoalkyl of 2-9 carbon atoms, N,N-dialkylaminoalkyl of 3-12 carbon atoms, N-cycloalkylaminoalkyl of 4-12 carbon atoms, N-cycloalkyl-N-alkylaminoalkyl of 5-18 carbon atoms, N,N-dicycloalkylaminoalkyl of 7-18 carbon atoms, morpholino-N-alkyl wherein the alkyl group is 1-6 carbon atoms, piperidino-N-alkyl wherein the alkyl group is 1-6 carbon atoms, N-alkyl-piperidino-N-alkyl wherein either alkyl group is 1-6 carbon atoms, azacycloalkyl-N-alkyl of 3-11 carbon atoms, hydroxyalkyl of 1-6 carbon atoms, alkoxyalkyl of 2-8 carbon atoms, carboxy, carboalkoxy of 1-6 carbon atoms, phenyl, carboalkyl of 2-7 carbon atoms, chloro, fluoro, and bromo; or a pharmaceutically acceptable salt thereof;

which process comprises (a) preparing an N-acyl-2-amino-4-alkoxy-5-nitrobenzoic acid compound by the process provided by the invention and (b) converting the N-acyl-2-amino-4-alkoxy-5-nitrobenzoic acid compound so prepared into a compound having formula I as defined and illustrated above or an acid addition salt thereof. X is preferably optionally substituted phenyl, particularly 3-chloro-4-fluorophenyl. The symbol n is preferably 0. Y is preferably —NH—. R$_3$ and RO— are preferably ethoxy. R$_2$ is preferably R$_8$—CH=CH—CO—NH— (in which R$_8$ is as defined above), R$_2$ being advantageously 4-(dimethylamino)but-2-enoyl-NH—. The compound of formula I is preferably N-{4-[(3-chloro-4-fluorophenyl)amino]-3-cyano-7-ethoxy-6-quinolinyl}-4-(dimethylamino)-2-butenamide.

The conversion of part (b) comprises using the acetylamino group at the 2-position and the carboxy group at the 1-position of the 2-(acetylamino)-4-alkoxy-5-nitrobenzoic acid as a precursor for a group of the formula II

(II)

(wherein X, Y and n are as defined above) and using the nitro group at the 5-position of the 2-(acetylamino)-4-alkoxy-5-nitrobenzoic acid as precursor for R$_2$. The formation of the group of the formula II may be carried out by cleaving the acetyl group from the acetylamino group, preferably under basic or acidic conditions, for instance, by a basic solvolysis, more preferably by alkaline alcoholysis, e.g. with KOH/MeOH, and using the resultant amino group and the carboxy group as precursor for a group of the formula II. The conversion of the amino group and carboxy group to the group of formula II may be carried out by known methods, for instance, by methods disclosed in U.S. Pat. No. 6,002,008. The conversion of the nitro group into R$_2$ may be carried out by reducing the nitro group to form an amino group and subjecting the amino group to amide formation by reaction with a carboxylic acid having the formula (R$_8$)$_2$—C=CR$_8$—COOH (in which each R$_8$ is as defined above) or a reactive derivative thereof, for instance the acid chloride having the formula (R$_8$)$_2$—C=CR$_8$—COCl. The conversion of the nitro group into R$_2$ may be carried out by methods known per se, for instance methods disclosed in U.S. Pat. No. 6,002,008. The formation of the group of the formula II is preferably carried out before the conversion of the nitro group into R$_2$. Thus part (b) preferably comprises (i) cleavage of the acyl group of the N-acyl-2-amino-4-alkoxy-5-nitrobenzoic acid compound so as to form a 2-amino-4-(C$_1$-C$_3$ alkoxy)-5-nitrobenzoic acid;

(ii) converting the 2-amino-4-(C$_1$-C$_3$ alkoxy)-5-nitrobenzoic acid into a nitro compound having formula I as illustrated above in which R, X, Y and n are as defined above and R$_2$ is nitro;

(iii) reducing this nitro compound so as to form an amino compound having formula I as illustrated above in which R, X, Y and n are as defined above and R$_2$ is amino; and (iv) subjecting this amino compound to amide formation by reaction with a carboxylic acid having the formula (R$_8$)$_2$—C=CR$_8$—COOH (in which each R$_8$ is as defined above) or a reactive derivative thereof.

The pharmaceutically acceptable salts are those derived from such organic and inorganic acids as: acetic, lactic, citric, tartaric, succinic, maleic, malonic, gluconic, hydrochloric, hydrobromic, phosphoric, nitric, sulfuric, methanesulfonic, and similarly known as acceptable acids.

DETAILED DESCRIPTION OF THE INVENTION

In accordance with this invention the production of N-acyl-2-amino-4-alkoxy-5-nitrobenzoic acids is provided in high yield and purity by a process which comprises:

(a) oxidizing N-(5-alkoxy-2-methyl-4-nitrophenyl)acetamides with potassium permanganate in the presence of magnesium sulfate in aqueous sulfolane (5-45% water) or aqueous pyridine at about 80 to 110° C.;

(b) acidifying the reaction mixture and collecting the product.

Preferred according to the process of the invention is a sulfolane:water volume ratio of about 19:1 to 1:1 v/v.

Preferred according to the process of the invention is a magnesium sulfate to potassium permanganate ratio of about 1:4 equivalents of magnesium sulfate to about 3:3.5 molar equivalents of potassium permanganate.

Preferred is acidifying the reaction mixture to a pH of about 2 to 6 and more preferably about 2 to 4.

Preferred is a reaction temperature of about 80-90° C.

Surprisingly, the use of sulfolane as a co-solvent in the oxidation of N-(5-alkoxy-2-methyl-4-nitrophenyl)acetamides allowed the reaction concentration to be more than doubled (20:1), minimized the amount of oxidant (3 to 3.5 molar equivalents) vs. 4 to 5 previously used under totally aqueous conditions and dramatically increasing the yield from 30 to 50% to at least 68 to 71% and further reducing the amount of inorganic waste. The use of sulfolane simplifies the isolation process by avoiding extraction procedures. A further advantage is that the process is very reproducible. A preferred procedure is to add solid potassium permanganate to a hot solution of N-(5-alkoxy-2-methyl-4-nitrophenyl)acetamides in the presence of magnesium sulfate in aqueous sulfolane at 80 to 90° C. An additional advantage of this procedure is that the oxidation may optionally be performed by adding the N-(5-alkoxy-2-methyl-4-nitrophenyl)acetamides as a sulfolane solution to the oxidizing mixture of potassium permanganate in water. The isolation of the product is accomplished by filtering the reaction mixture to remove inorganics, followed by diluting the filtrate with water and acidifying the reaction mixture to about pH 2 to 4. The product precipitates and is collected by filtration. Similar results are obtained using aqueous pyridine as the solvent. Preferred cosolvents are sulfolane and pyridine.

In order to facilitate a further understanding of the invention, the following non-limiting examples illustrate the process of the present invention.

EXAMPLE 1

2-Acetylamino-4-Ethoxy-5-Nitrobenzoic Acid

A 5-L Morton flask equipped with an overhead stirrer and thermocouple is charged with N-(5-ethoxy-2-methyl-4-nitro-phenyl)-acetamide (46 g, 193 mmol), aq. sulfolane (95:5 v/v, 500 mL) and water (200 mL). The reaction mixture is heated to 90° C. and then magnesium sulfate ($MgSO_4$) (46 g, 382 mmol) and water (200 mL) are added to the reaction mixture. The potassium permanganate ($KMnO_4$) (105 g, 670 mmol) is added in 15-g portions every 15 minutes until the reaction is complete by HPLC [>95%]. Retention time $T_r$ of N-(5-ethoxy-2-methyl-4-nitro-phenyl)-acetamide is 10.7 min and $T_r$ of 2-acetylamino-4-ethoxy-5-nitro-benzoic acid is 12.4 min in a 65:35 mixture of $CH_3CN$ with 0.1% trifluoroacetic acid (TFA):$H_2O$ run isocratically at 1.0 mL/min with a Phenomenex Prodigy 5 ODS column (250×4.6 mm). The hot solution (>80° C.) is filtered thru diatomaceous earth (6" diameter and 1" thick) and the filter cake ($MnO_2$) is rinsed with hot water (>80° C., 3×200 mL). While stirring the filtrate, 10% HCl is added until the pH is adjusted to about 2 to 4 and stirring of the suspension continued while cooling to ambient temperature (15 to 25° C.). The suspension is filtered with a fritted funnel (medium) and the filter cake is washed with water (3×200 mL). The cake is dried to constant weight under vacuum (50 mm Hg) at 40 to 50° C. This procedure provides product of high purity in good yield (36.5 g, 70% yield, >98% purity by NMR integration). $^1$H NMR (300 MHz, DMSO-$d_6$) 11.5 (br s, 1H), 8.52 (s, 1H), 8.50 (s, 1H), 4.22 (q, j=7 Hz, 2H), 2.21 (s, 3H), 1.40 (t, j-7 Hz, 3H)

EXAMPLE 2

2-Acetylamino-4-Ethoxy-5-Nitrobenzoic Acid

A 500 mL Morton flask equipped with an overhead stirrer and thermocouple is charged with N-(5-ethoxy-2-methyl-4-nitro-phenyl)-acetamide (3 g, 12.5 mmol) and aq. sulfolane (95:5 v/v, 35 mL). While stirring is added $MgSO_4$ (5 g, 41.5 mmol) and water (15 mL). The reaction mixture is heated to 90-95° C. and 125 mL (31.2 mmol, 2.4 eq) of a 0.25M aqueous solution of $KMnO_4$ is added at a rate to control exothermic foaming. The reaction is complete in about 15 to 20 minutes by HPLC [>95%]. Retention time $T_r$ of N-(5-ethoxy-2-methyl-4-nitro-phenyl)-acetamide is 10.7 min and $T_r$ of 2-acetylamino-4-ethoxy-5-nitro-benzoic acid is 12.4 min in a 65:35 mixture of $CH_3CN$ with 0.1% TFA:$H_2O$ run isocratically at 1.0 mL/min with a Phenomenex Prodigy 5 ODS column (250×4.6 mm). However, should the reaction be incomplete, as shown by HPLC system above, additional portions of the $KMnO_4$ (25 mL, 6.25 mmol) are added at 15-20 minute intervals and completion monitored by HPLC as above. The hot solution (>80° C.) is filtered through diatomaceous earth (6" diameter and 1" thick) and the filter cake ($MnO_2$) is rinsed with hot water (>80° C., 3×200 mL). While stirring the filtrate, 10% HCl is added until the pH is adjusted to about 2 to 4 and stirring of the suspension continued while cooling to ambient temperature (15 to 25° C.). The suspension is filtered with a fritted funnel (medium) and the filter cake is washed with water (3×200 mL). The cake is dried to constant weight under vacuum (50 mm Hg) at 40 to 50° C. This procedure provides product of high purity in good yield; 2.4 g, 71%, purity >98% by NMR integration or by HPLC.

EXAMPLE 3

2-Acetylamino-4-Ethoxy-5-Nitrobenzoic Acid

In a 5-L multi-neck flask, equipped with mechanical stirrer, thermometer and condenser is charged with water (1500 mL) followed by $MgSO_4$ (67 g). To the resulting solution is added pyridine (500 mL) and then N-(5-ethoxy-2-methyl-4-nitro-phenyl)-acetamide (50 g) over 5 min. The suspension is heated to 85° C. and the resulting solution is charged with $KMnO_4$ (150.0 g) over 20 min until the reaction is complete by HPLC [>95%]. Retention time $T_r$ of N-(5-ethoxy-2-methyl-4-nitro-phenyl)-acetamide is 7.5 min and $T_r$ of 2-acetylamino-4-ethoxy-5-nitrobenzoic acid is 8.5 min) in a 40:60 mixture of $CH_3CN$ with 0.1% $H_3PO_4$:$H_2O$ run isocratically at 1.0 mL/min with a Phenomenex Luna C8 column (150×4.6 mm). Upon completion, the hot mixture (80 to 85° C.) is filtered on a Buchner (20 cm diameter). The filter cake (MnO$_2$) is washed with hot water (850 mL). The filtrates are combined, cooled to 30° C. and treated with conc. HCl (125 mL) to pH=6. The resulting suspension is stirred at 30° C. for 30 min and the product is collected on a Buchner funnel (20 cm diameter). The cake is suspended in water (500 mL) and treated with conc. HCl (11 mL) to pH=1.5. The product is collected on a Buchner funnel (16 cm diameter) and washed with water (100 mL) followed by acetone (50 mL). The cake is dried to constant weight under vacuum (10 mm Hg) at 65° C. This procedure provides product of high purity in good yield (38.5 g, 68.4%, 98.7% purity by HPLC). $^1$H NMR (400 MHz, DMSO-d$_6$): 11.5 (br s, 1H), 8.52 (s, 1H), 8.50 (s, 1H), 4.22 (q, j=7 Hz, 2H), 2.21 (s, 3H), 1.40 (t, j-7 Hz, 3H)

What is claimed is:

1. A process for the preparation of a N-acyl-2-amino-4-alkoxy-5-nitrobenzoic acid compound having the structural formula

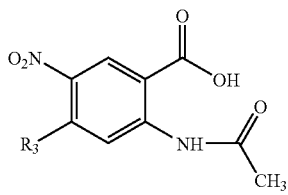

wherein:
R$_3$ is —OR; and
R is alkyl of 1 to 3 carbon atoms;
which process comprises:
oxidizing a N-(5-alkoxy-2-methyl-4-nitrophenyl)acetamide compound having the structural formula

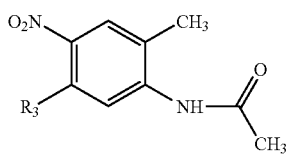

where
R$_3$ is —OR; and
R is alkyl of 1 to 3 carbon atoms;
with potassium permanganate in solution in a solvent system comprising water and a cosolvent in the presence of magnesium sulfate at a specified reaction temperature.

2. The process of claim 1 wherein potassium permanganate is present in the amount of about 3 to 3.5 molar equivalents.

3. The process of claim 1 wherein the cosolvent is aqueous sulfolane.

4. The process of claim 3 wherein the sulfolane to water ratio is present at about 19:1 to 1:1.

5. The process of claim 1 wherein the cosolvent is aqueous pyridine.

6. The process of claim 1 wherein the ratio of magnesium sulfate to potassium permanganate is about 1:4 equivalents of magnesium sulfate to about 3:3.5 molar equivalents of potassium permanganate.

7. The process of claim 1 wherein the reaction temperature is about 80 to 110° C.

8. The process of claim 7 wherein the reaction temperature is about 80-90° C.

9. A process for the preparation of a N-acyl-2-amino-4-alkoxy-5-nitrobenzoic acid compound having the structural formula

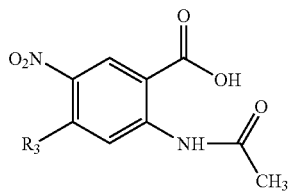

wherein:
R$_3$ is —OR; and
R is alkyl of 1 to 3 carbon atoms;
which process comprises the steps:
a.) heating to 80-90° C. an aqueous solution, containing sulfolane as a cosolvent, and a N-(5-alkoxy-2-methyl-4-nitrophenyl)acetamide compound having the structural formula

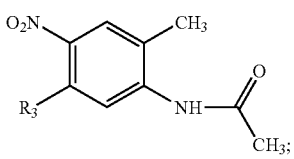

wherein:
R$_3$ is —OR; and
R is alkyl of 1 to 3 carbon atoms;
b.) adding magnesium sulfate to the aqueous solution;
c.) adding sufficient potassium permanganate to the aqueous solution to complete oxidation;
d.) filtering the hot solution;
e.) acidifying the solution to a pH of about 2 to 4 with cooling and collecting the N-acyl-2-amino-4-alkoxy-5-nitrobenzoic acid.

10. The process of claim 9 wherein potassium permanganate is present in the amount of about 3 to 3.5 molar equivalents.

11. The process of claim 9 wherein the sulfolane to water ratio is present at about 19:1 to 1:1.

12. The process of claim 9 wherein the ratio of magnesium sulfate to potassium permanganate is present in the amount of about 1:4 equivalents of magnesium sulfate to about 3:3.5 molar equivalents of potassium permanganate.

* * * * *